United States Patent [19]
Hendriksen et al.

[11] Patent Number: 6,002,057
[45] Date of Patent: *Dec. 14, 1999

[54] ALKYLATION PROCESS USING ZEOLITE BETA

[75] Inventors: Dan Eldon Hendriksen, Kingwood; James Richardson Lattner, Seabrook, both of Tex.; Mechilium Johannes Gerardus Janssen, Leuven, Belgium

[73] Assignee: Exxon Chemical Patents Inc., Houston, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/925,812

[22] Filed: Sep. 5, 1997

Related U.S. Application Data

[60] Provisional application No. 60/025,577, Sep. 6, 1996.

[51] Int. Cl.$^6$ .............................. C07C 1/00; C07C 2/68; C07C 2/64
[52] U.S. Cl. ......................... 585/448; 585/467; 585/323; 203/DIG. 6
[58] Field of Search ...................... 585/448, 467, 585/256, 258, 259, 260, 264, 265, 323; 203/28, 29, 71, DIG. 6

[56] References Cited

U.S. PATENT DOCUMENTS

| | | | |
|---|---|---|---|
| Re. 28,341 | 2/1975 | Wadlinger et al. | 208/120 |
| 3,308,069 | 3/1967 | Wadlinger et al. | 252/455 |
| 3,310,592 | 3/1967 | Fukuda et al. | 260/672 |
| 4,215,011 | 7/1980 | Smith, Jr. | 252/426 |
| 4,302,356 | 11/1981 | Smith, Jr. | 252/426 |
| 4,440,871 | 4/1984 | Lok et al. | 502/214 |
| 4,443,559 | 4/1984 | Smith, Jr. | 502/527 |
| 4,508,837 | 4/1985 | Zones | 502/62 |
| 4,891,458 | 1/1990 | Innes et al. | 585/323 |
| 5,081,323 | 1/1992 | Innes et al. | 585/449 |
| 5,082,990 | 1/1992 | Hsieh et al. | 585/467 |
| 5,118,896 | 6/1992 | Steigelmann et al. | 585/467 |
| 5,273,644 | 12/1993 | Wegerer | 208/66 |
| 5,275,790 | 1/1994 | Buchholz et al. | 422/217 |
| 5,496,446 | 3/1996 | Yeoman et al. | 202/158 |
| 5,602,290 | 2/1997 | Fallon | 585/448 |

FOREIGN PATENT DOCUMENTS

| | | |
|---|---|---|
| 0 055 046 A1 | 6/1982 | European Pat. Off. . |
| 0 064 328 | 11/1982 | European Pat. Off. . |
| 0 095 304 | 11/1983 | European Pat. Off. . |
| 0 159 846 | 10/1985 | European Pat. Off. . |
| 0 159 847 | 10/1985 | European Pat. Off. . |
| 0 164 939 | 12/1985 | European Pat. Off. . |
| 432 814 A1 | 6/1991 | European Pat. Off. . |
| 467007 | 4/1992 | European Pat. Off. . |
| 0 571 701 | 12/1993 | European Pat. Off. . |
| 629 599 A1 | 12/1994 | European Pat. Off. . |
| 633872 | 1/1995 | European Pat. Off. . |
| 2 024 790 | 1/1980 | United Kingdom . |
| WO 93/13013 | 7/1993 | WIPO . |

*Primary Examiner*—Walter D. Griffin
*Assistant Examiner*—Thuan D. Dang
*Attorney, Agent, or Firm*—James A. Zboray

[57] ABSTRACT

A process for the alkylation of an aromatic compound with $C_2$ to $C_4$ olefin alkylating agent. A process to produce ethylbenzene by reaction of ethylene in stoichiometric or excess amount with benzene in the presence of a zeolite beta catalyst. This process is especially suitable for reaction of dilute ethylene with dilute benzene in a catalytic distillation column.

45 Claims, 2 Drawing Sheets

ALKYLATION PROCESS USING ZEOLITE BETA

This application claims the benefit of U.S. provisional Application No. 60/025,577 filed on Sep. 6, 1996.

FIELD OF THE INVENTION

This invention relates to a process for the alkylation of an aromatic hydrocarbon with an olefin alkylating agent. Specific embodiments relate to a process for manufacturing ethylbenzene from a composition containing benzene and another composition containing ethylene. Ethylbenzene is used commercially primarily as a raw material in the manufacture of styrene. Another embodiment relates to a process for manufacturing cumene from a composition containing benzene and another composition containing propylene. Cumene is used as a raw material in the manufacture of phenol.

BACKGROUND OF THE INVENTION

This invention is a process for the alkylation of an aromatic hydrocarbon which comprises contacting the aromatic hydrocarbon with a stoichiometric or excess amount of a $C_2$ to $C_4$ olefin alkylating agent and in the presence of a catalyst comprising zeolite beta. This is especially useful for the production of a mixture of ethylbenzene and diethylbenzene by the reaction of dilute ethylene with dilute benzene. It can be carried out in a fixed bed reactor or more preferably in a catalytic distillation reactor.

The known processes for the manufacture of ethylbenzene use the Friedel-Crafts reaction of alkylation of benzene by ethylene. Similarly, Friedel-Crafts reaction of alkylation of benzene by propylene is used to manufacture cumene.

The catalysts for this reaction are typically Bronsted or Lewis acids, including aluminum chloride, boron trifluoride deposited on alumina, or zeolites used in liquid or gas phase.

One of the difficulties encountered in this reaction is for example when ethylene is used as the alkylating agent that the ethylbenzene formed is more reactive than benzene with respect to ethylene, which leads to the production of diethylbenzenes, which are themselves more reactive than ethylbenzene, and therefore have a tendency to form triethylbenzenes. To limit these polyalkylation reactions, the prior art teaches the use of a large excess of benzene with respect to the ethylene at the entry of the alkylation reactors. Thus, the benzene/ethylene molar ratio is generally between 2 and 2.5 for the processes using aluminum chloride, and the ratio may even reach a value between 8 and 16 for processes using zeolites in the gas phase. In spite of the use of an excess of benzene with respect to the ethylene to minimize the formation of polyethylbenzenes, such formation cannot be completely avoided.

It is becoming increasingly desirable to be able to economically remove the majority of the benzene from streams being blended into gasoline to meet environmental regulations. Prior art describes means to accomplish this by alkylating, the benzene. Such approaches while successfully reducing the benzene contained in the gasoline by converting it to higher boiling alkyl benzenes, typically do not remove the aromatic rings. Therefore, total aromatic content in the gasoline remains essentially unchanged. Environmental regulations for gasoline and distillate fuels are increasingly limiting both the benzene and total aromatic content. Therefore from an environmental standpoint it is more desirable to remove the benzene ring from the gasoline.

It is also economically attractive to make use of the benzene in such streams as a feedstock in processes that make high-valued petrochemicals such as ethylbenzene and cumene instead of requiring a purified benzene stream as the feedstock, as is now practiced in the industry.

U.S. Pat. No. 4,891,458 discloses: a process for the alkylation of an aromatic hydrocarbon which comprises contacting the aromatic hydrocarbon with a $C_2$ to $C_4$ olefin under at least partial liquid phase conditions and in the presence of a catalyst comprising zeolite beta. (column 2, lines 33–39). This same patent further discloses, "When alkylation is the process conducted according to this invention, reaction conditions are as follows. The aromatic hydrocarbon feed should be present in stoichiometric excess. It is preferred that the molar ratio of aromatics to olefins be at least about four to one (4:1) to prevent rapid catalyst fouling." (column 5, lines 24–29). In U.S. Pat. No. 5,081,323, a continuation of U.S. Pat. No. 4,891,458, feeding a part of the aromatic stream between reactor beds is disclosed.

Published EP-A-571,701 discloses a process for alkylating a hydrogenated dilute benzene with a dilute olefin stream. The dilute benzene is first hydrogenated in order to remove $C_5$–$C_7$ olefins. Zeolite beta is specifically disclosed as a suitable catalyst. The molar ratio of aromatics to olefins is required to be at least about three to one (3:1). Further, the aromatic hydrocarbon feed should be present in a stoichimetric excess, and it is preferred that the molar ratio of aromatics to olefins be at least 3:1 to prevent catalyst fouling (page 6. lines 42–44).

In the prior art thus far discussed, a stoichimetric excess of benzene is employed, this can easily be achieved when commercially pure benzene is used as a feedstock. In this instance as is well known in the arts, the unreacted benzene is recovered downstream by distillation and merely recycled back to the reactor. This maintains the stoichimetric excess of benzene in the alkylation reactor feed and achieves high ultimate conversion of benzene. However, when the feed stream is dilute in benzene, high conversion of the benzene is not so easily achievable, when a stoichiometric excess is required by the process. In this latter situation the unreacted benzene will be diluted with materials not easily separated by distillation, and therefore would rapidly build up if the stream containing them were recycled to the alkylation reactor. A common approach to avoid this undesirable result is to purge a significant fraction of the steam containing the unreacted benzene, which necessarily results in a relatively low ultimate conversion of the benzene originally in the feedstream.

For the foregoing reasons there is a need for a process which is able to remove the benzene from hydrocarbon streams in the gasoline boiling range, which at the same time does not require the use of excess benzene, achieves a high level of benzene removal, can use dilute ethylene or propylene as an alkylating agent, and allows for the recovery of high valued petrochemical products such as ethylbenzene or cumene.

SUMMARY OF THE INVENTION

The present invention is directed towards a process that satisfies the need of being able to produce ethylbenzene from streams dilute in benzene and dilute in ethylene. Specifically, the present invention is directed towards a process for the alkylation of an aromatic hydrocarbon which comprises contacting the aromatic hydrocarbon with a stoichimetric or excess amount of at least one olefin alkylating agent selected from the group consisting of ethylene, propylene or butylene, in the presence of a catalyst comprising zeolite beta.

More specifically, a process for the alkylation of an aromatic hydrocarbon contained in a hydrocarbon stream comprising: processing the hydrocarbon stream to substantially remove all but one aromatic compound; treating the hydrocarbon stream to remove essentially all olefinic compounds; contacting said hydrocarbon stream with a stream comprising at least one olefin, wherein the molar ratio of said olefin to said aromatic is equal or greater than 1, in the presence of a catalyst comprising zeolite beta, under alkylation conditions, whereby mono and polyalkylated aromatics are formed; separating the mono and poly alkylated aromatics formed in the alkylation reaction from the remaining hydrocarbons.

Another embodiment is a process for ethylating benzene contained in a hydrocarbon stream comprising: processing the hydrocarbon stream to remove substantially all aromatics other than benzene from the hydrocarbon stream, treating the hydrocarbon stream to remove essentially all olefinic compounds, contacting said hydrocarbon stream with a stream comprising ethylene wherein the molar ratio of ethylene to benzene is equal or greater than 1, in the presence of a catalyst comprising zeolite beta under alkylation conditions, whereby ethyl benzene and polyethyl benzenes are formed, separating the ethyl benzene and polyethyl benzenes formed in the alkylation reaction from the remaining hydrocarbons. The product ethyl benzene can then be separated from the poly ethyl benzenes.

In another embodiment the benzene contained in a reformate heartcut is ethylated by treating the reformate with hydrogen to convert essentially all olefinic compounds to paraffins, contacting the reformate heartcut with a stream comprising ethylene and essentially no other olefin wherein the molar ratio of ethylene to benzene is greater than 1 in the presence of a catalyst comprising zeolite beta under alkylation conditions whereby mono and polyethylbenzenes are formed, separating the ethyl benzene and polyethylbenzes formed from the remaining hydrocarbons and separating the ethylbenzene from the polyethylbenzene.

In another embodiment processing the hydrocarbon stream to remove substantially all aromatics other than benzene from the hydrocarbon stream; treating the hydrocarbon stream to remove essentially all olefinic compounds; contacting the thus treated hydrocarbon stream with a stream comprising propylene wherein the molar ratio of propylene to benzene is equal to or greater than 1, in the presence of a catalyst comprising zeolite beta under alkylation conditions, whereby mono and polyisopropyl-benzene are formed; separating the mono and polyisopropylbenzene formed from the remaining hydrocarbons.

These and other features, aspects, and advantages of the present invention will become better understood with reference to the following drawings, description, and appended claims.

The following description covers a preferred embodiment wherein the aromatic hydrocarbon is benzene and the olefin alkylating agent is ethylene. One skilled in the art will recognize that substantially similar flowsheets will apply to embodiments wherein different aromatic hydrocarbons and olefin alkylating agents are used. One specific such embodiment is the production of cumene wherein the aromatic hydrocarbon is benzene and the olefin alkylating agent is propylene.

Figure 1:
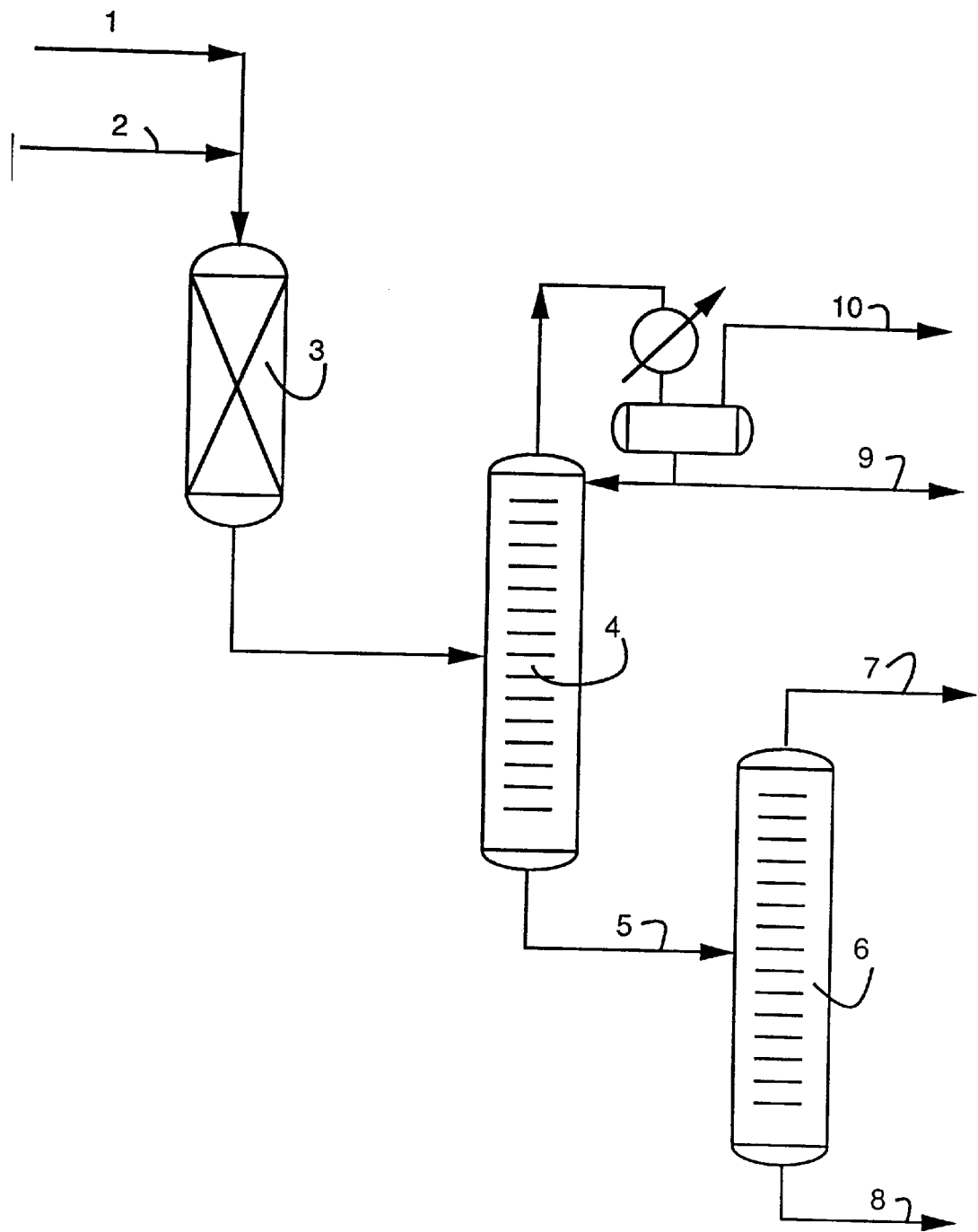
FIG. 1 shows an embodiment where the alkylation takes place in a fixed bed or moving bed reactor.

In FIG. 1 the benzene containing stream (1) and the ethylene containing stream (2) are fed to a fixed or moving bed alkylation reactor (3). The unreacted low boiling materials such as ethylene, hydrogen, methane, ethane, benzene, and $C_6$–$C_7$ paraffins are removed in the overhead of a first distillation column (4). The bottoms of that column contain the product ethylbenzene and the polyalkylated benzene (5). The bottoms stream containing the product ethylbenzene and the polyalkylated benzene is separated by distillation in a second column (6) into product ethylbenzene (7) which goes overhead and the poly alkylated benzenes (8) which are in the bottoms. These polyalkylated benzenes can be converted to additional ethylbenzene by transalkylation as discussed in the detailed description of the invention.

The overhead from the first column is split into a liquid distillate (9) and a vapor distillate (10). The vapor distillate contains the unreacted ethylene from the ethylene-containing stream, which, if desired, may be recovered by reaction with pure benzene in a second reactor or catalytic distillation tower. The condensed overhead also called liquid distillate from the first distillation column contains the unreacted $C_5$–$C_7$ paraffins and a small amount of unreacted benzene. A special feature of this invention is that use of a molar excess of ethylene results in very high conversion of benzene such that a very small percentage of the benzene contained in the benzene-containing feed stream is unreacted. This stream may be advantageously added to the gasoline pool, having been largely depleted of benzene. A small stabilization tower may be required to strip off any remaining light materials.

Figure 2:
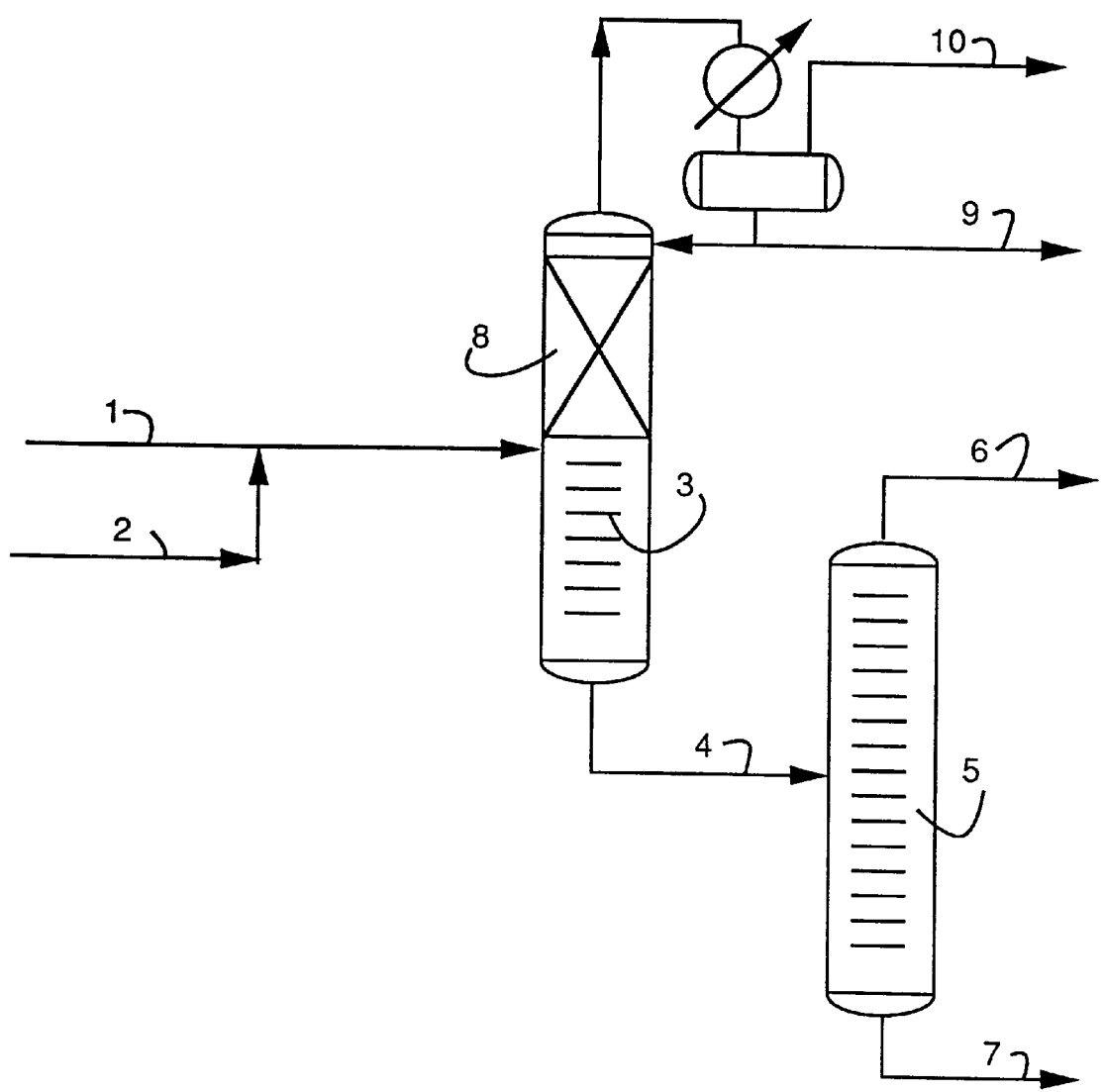
FIG. 2 shows an embodiment where the alkylation takes place in a catalyst bed within a catalytic distillation reactor. Additional distillations are required in either case to recover the product alklybenzene.

In FIG. 2, where the reaction is carried out in a catalytic distillation column, the benzene-containing stream (1) and the ethylene-containing stream (2) are fed directly to the catalytic distillation column.

In this case shown in FIG. 2 the first separation takes place in the same distillation column (3) where the catalyst (8) is placed. Similar to the case shown in FIG. 1. The bottoms stream containing the product ethylbenzene and the polyalkylated benzenes (4) is separated in a distillation column (5) into product ethylbenzene (6) which goes overhead and the polyalkylated benzenes (7) which are in the bottoms. These polyalkylated benzenes can be converted to additional ethylbenzene by transalkylation as discussed in the detailed description of the invention.

The overhead of the first column (3) contains a vapor of distillate (10) and a liquid distillate (9). The vapor distillate contains the unreacted ethylene from the ethylene-containing stream which, if desired may be recovered by reaction with pure benzene in a second reactor or catalytic distillation tower. The condensed overhead also called liquid distillate from the catalytic distillation column as the case may be contains the unreacted $C_5$–$C_7$ paraffins and the small amount of unreacted benzene. A special feature of this invention is that use of a molar excess of ethylene results in high conversion of benzene such that a very small percentage of the benzene contained in the benzene-containing feed stream is unreacted. This stream may be added advantageously to the gasoline pool. A small stabilization tower may be required to strip off any remaining light materials.

DETAILED DESCRIPTION OF THE INVENTION

This invention is a process for the alkylation of an aromatic hydrocarbon which comprises contacting the aromatic hydrocarbon with a stoichiometric or excess amount of at least one $C_2$ to $C_4$ olefin alkylating agent in the presence of a catalyst comprising zeolite beta. This is especially useful for the production of a mixture of ethylbenzene and diethylbenzene by the reaction of dilute ethylene with dilute benzene. A light reformate heartcut is an especially preferred feed. A preferred embodiment carries out the reaction in a catalytic distillation reactor. The process, when carried out in a catalytic distillation reactor, is intended to result in a high conversion of both ethylene and benzene when they are present in near stoichiometric amounts, and in a high conversion of benzene when the ethylene is present in excess. The inert diluents in the $C_2$ stream (e.g., hydrogen, methane, ethane, etc.) and in the $C_6$ stream (hexanes) are distilled away from the product ethylbenzene, diethylbenzene, and the polyethyl benzene in the catalytic distillation reactor. The product ethylbenzene is recovered by further distillation. The diethylbenzene and other polyethyl benzenes can be converted to ethylbenzene by transalkylation with additional benzene in a conventional manner.

The prior art teaches that an excess of aromatic over olefin must be present in order (1) to prevent excessive multiple alkylation of the aromatic, and (2) to prevent the rapid fouling and deactivation of solid catalysts. We have surprisingly found that a zeolite beta catalyst shows stable activity with stoichiometric or excess olefin and the zeolite beta catalyst also limits the extent of the multiple alkylation. Naturally, with an excess of olefin, some multiple alkylation is inevitable, but we also have surprisingly found that the multiple alkylation is directed primarily towards diethylbenzene.

Since the present invention is directed towards the production of high valued, high purity products, it is especially important to process the hydrocarbon feed stream to remove essentially all of the aromatic species other than the aromatic species which it is desired to alkylate. This prevents the formation of an undesirable mixture of alkylated aromatic compounds. This process may be accomplished by distillation of the hydrocarbon feed stream, for example in two steps, one distillation removing lower boiling components and another removing higher boiling components. This process is known in the art as making a heartcut.

Examples of suitable aromatic hydrocarbon feedstocks which may be alkylated by the process of the invention are streams including aromatic compounds such as benzene, toluene, xylene, and naphthalene. In each case the hydrocarbon feedstream is processed so that essentially only one of the aromatic compounds is present. A preferred aromatic hydrocarbon feedstock contains benzene.

The benzene feedstream may be pure benzene or diluted benzene containing at least 10 wt % benzene. The stream preferably contains at least 20 wt. % benzene and more preferably at least 30 wt.% benzene. Advantageously, the alkylation reaction is industrially feasible with the present invention with the use of a benzene feedstock stream also containing saturated hydrocarbons diluting the benzene which is present.

Advantageously, the benzene feedstream containing diluted benzene in saturated hydrocarbons is a light reformate coming from a crude oil refinery. The possibility of using these generally abundant light reformates and eliminating nearly all their benzene content makes available gasolines which fulfill current regulations.

It is also important to treat the hydrocarbon stream containing the aromatic to be alkylated to remove reactive compounds such as olefins that would otherwise participate in the alkylation reaction and produce undesirable byproducts. A preferred means to remove the reactive olefinic compounds is to hydrogenate them to paraffins. Suitable hydrogenation catalysts useful in practicing the present invention include nickel, nickel molybdenum, cobalt molybdenum or palladium catalysts which can be deposited on a support. When used, the support is preferably alumina, silica, or alumina-silica. Alumina is the most preferred support. Conditions typically employed for this purpose are known in the art.

In one embodiment of the present invention, the $C_5$–$C_7$ olefins present in a light reformate are hydrogenated in the presence of a hydrogenation catalyst. Preferred catalysts include palladium catalysts deposited on alumina. Preferred hydrogenation reaction conditions are as follows. The hydrogen/$C_5$–$C_7$ olefins molar ratio is comprised between 1 and 4. The reaction temperature is generally in the range of from 50° C. to 150° C., and preferably from 80° C. to 120° C. The reaction pressure is typically about 1 MPa. Contact time may range from 10 s to 10 h but is usually from 1 min to 1 h. The weight hourly space velocity (WHS.), in terms of grams of reformate per gram of catalyst per hour, is generally in the range of from 1 to 50.

In another embodiment of the present invention, the $C_5$–$C_7$ olefins present in pyrolysis gasoline are hydrogenated in the presence of a hydrogenation catalyst. Preferred catalysts include cobalt-molybdenum catalysts. Preferred hydrogenation reaction conditions are as follows. The hydrogen/$C_5$–$C_7$ olefins molar ratio is comprised between 5 and 25. The reaction temperature is generally in the range of from 150° C. to 250° C., and preferably from 200° C. to 220° C. The reaction pressure is typically about 4 MPa. Contact time may range from 10 s to 10 h but is usually from 1 min to 1 h. The weight hourly space velocity (WHSV), in terms of grams of reformate per gram of catalyst per hour, is generally in the range of from 1 to 50.

In accordance with the present invention, various types of reactors can be utilized for the hydrogenation step. For example, the hydrogenation can be carried out in a fixed bed reactor in an upflow or downflow mode.

Suitable olefins for the alkylation of the aromatic hydrocarbon are those containing 2 to 4 carbon atoms, such as ethylene, propylene, butene-1, trans-butene-2 and cis-butene-2, or mixtures thereof. Preferred olefins are ethylene and propylene. An especially preferred olefin is ethylene. These olefins may be present in admixture with hydrogen, methane, $C_2$ to $C_4$ paraffins, but it is usually preferable to remove dienes, acetylenes, sulfur compounds or basic nitrogen compounds (NH3 or amines) which may be present in the olefin feedstock stream, to prevent rapid catalyst deactivation.

The ethylene feedstream may be a distillation fraction of the gas from a fluid catalytic cracking unit or from a steam cracker containing hydrocarbons having 2 or fewer carbons. The ethylene feedstream may be pure ethylene or diluted ethylene containing preferably at least 10 wt % ethylene. The stream more preferably contains at least 20 wt. % ethylene and most preferably at least 30 wt. % ethylene. A preferable source of ethylene from a cat cracker is the deethanizer overhead, sometimes called the "dry gas". A preferable source of ethylene from a steam cracker would be the feedstream to the ethylene/ethane splitter also called the $C_2$ splitter.

Advantageously, the ethylene feedstock stream is diluted in saturated hydrocarbons, while unsaturated hydrocarbons other than ethylene have been removed. Thus, the absence of propylene, for example, simplifies the composition of the alkylate obtained and allows an easy separation of its constituents, particularly by one or more distillation operations.

When the alkylation process is conducted according to this invention, reaction conditions are described as follows. A special feature of the present invention is that the olefinic feed should be present in stoichiometric excess over the aromatic compound sought to be alkylated.

The molar ratio of olefins to aromatics should be at least stoichiometric. It is preferred that the molar ratio of olefins to aromatics be 1–5. More preferably the molar ratio of olefins to aromatics is from 1.1 to 3. The reaction temperature may range from 100° F. to 600° F., preferably, 250° to 450° F. In the case of cumene production, a temperature range of 250° F. to 375° F. is most preferred to reduce product impurities. The reaction pressure should be sufficient to maintain at least a partial liquid phase in order to retard catalyst fouling. This is typically 50 to 1000 psig depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

Various types of reactors can be used in the alkylation process of this invention. For example, the process can be carried out in batchwise fashion by adding the catalyst and aromatic feedstock to a stirred autoclave, heating to reaction temperature, and then slowly adding the olefinic feedstock to reach molar excess of olefin. A heat transfer fluid can be circulated through the jacket of the autoclave, or a condenser can be provided to remove the heat of reaction and maintain a constant temperature. Large scale continuous industrial processes may employ a fixed bed reactor operating in an upflow or downflow mode or a moving bed reactor operating with concurrent or countercurrent catalyst and hydrocarbon flows. These reactors may contain a single catalyst bed or multiple beds and may be equipped for the interstage addition of olefins or olefin containing streams and interstage cooling. Interstage olefin addition and more nearly isothermal operation enhance product quality and catalyst life. A moving bed reactor makes possible the continuous removal of spent catalyst for regeneration and replacement by fresh or regenerated catalysts.

A catalytic distillation column is an especially suitable device for carrying out the alkylation process of this invention. It is especially preferred when dilute olefin and dilute aromatic feedstreams are used.

The catalytic distillation structure provides both the catalytic sites and the distillation sites. The alkylated benzene product is withdrawn from the distillation column reactor at a point below the catalyst bed and the unreacted aromatic feedstream compound may be taken off as an overhead.

More specifically the catalyst is contained in a packed bed of a nature as to allow vapor flow through the bed, yet provide a sufficient surface area for catalytic contact. Numerous examples of this type of packing are known in the art. Some examples are U.S. Pat. Nos. 4,443,559, 4,215,011, 4,302,356, 5,496,446, and 5,275,790 which are incorporated by reference herein in their entirety. The catalyst packing is preferably arranged in the upper portion of the distillation column reactor. It may occupy about one-third to one half of the column and extending substantially to the upper end thereof.

The olefin (e.g., ethylene) feed to the reaction preferably enters below the catalyst bed thereby allowing mixing of the reactants before contact with the catalyst bed. In another embodiment the olefin feed to the reaction preferably enters into the catalyst bed, such as between the bottom of the fixed bed, and the upper one-fourth section thereof preferably in the middle one-half of the bed.

The dilute benzene also enters below the bed. No benzene is added to the upper portion of the tower or to the reflux stream.

The alkylated product is the highest boiling material and is separated in the lower portion of the column, usually as bottoms. The non-aromatic compounds present in the stream containing the benzene and the unreacted components in the olefin feed leave overhead.

The use of a catalytic distillation apparatus offers several advantages in the practice of the invention. First, because the reaction occurs concurrently with distillation, the reaction product is removed from the reaction zone as it is formed. The removal of the alkylation product helps to minimize polyalkylation of the alkylation products. Second, because the aromatic compound is boiling, the temperature of the reaction is controlled by the boiling point of that component at the system pressure. The heat of the reaction simply creates more vapor, but no increase in temperature.

A preferred catalyst for practicing the invention is zeolite beta. Zeolite beta is a known synthetic crystalline aluminosilicate originally described in U.S. Pat. Nos. 3,308,069 and Re 28,341, to which reference is made for further details of this zeolite, its preparation and properties and which is incorporated herein by reference. Zeolite beta is identified by its characteristic X-ray diffraction pattern, which is set out in Table 4 of U.S. Pat. Nos. 3,308,069 and Re 28,341. This pattern, in terms of the significant d values (Angstroms, radiation: K alpha doublet of copper, Geiger counter spectrometer), is reproduced in Table 1 below.

TABLE 1

| d Values of Reflection in Zeolite Beta |
| --- |
| 11.4 ± 0.2 |
| 7.4 ± 0.2 |
| 6.7 ± 0.2 |
| 4.25 ± 0.1 |
| 3.97 ± 0.1 |
| 3.0 ± 0.1 |
| 2.2 ± 0.1 |

U.S. Pat. Nos. 3,308,069 and Re 28,341 describe the composition of zeolite beta in its as-synthesized form as follows:

$[X\text{Na}(1.0\pm0.1-X)\text{TEA}]\text{AlO}_2 \cdot Y\ SiO_2 \cdot W\ H_2O$ wherein X is less than 1, preferably less than 0.75, TEA represents tetraethylammonium ion, Y is greater than 5 and less than 100, and W is up to about 4, depending on the condition of dehydration and on the metal cation present. These patents also teach that the sodium may be replaced by another metal ion using ion exchange techniques.

Subsequent publications such as European Patent Applications Nos. 95,304, 159,846, 159,847, and 164,939 have broadened the definition of zeolite beta to include materials prepared using templating agents other than tetraethylammonium hydroxide and materials having Si/Al atomic ratios greater than 100. Also, the zeolites described in European Patent Applications Nos. 55,046 ("Nu-2") and 64,328 and British Patent Application No. 2,024,790 ("Boralite B") have structures and X-ray diffraction patterns very similar to that of zeolite beta and are included within the scope of the term "zeolite beta", as used herein.

The forms of zeolite beta which are most useful in the present invention are crystalline aluminosilicates having the empirical formula:

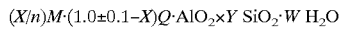
$(X/n)M \cdot (1.0 \pm 0.1 - X)Q \cdot AlO_2 \cdot xY \, SiO_2 \cdot W \, H_2O$ wherein X is less than 1, preferably less than 0.75, Y is greater than 5 and less than 100, W is up to about 4, M is a metal ion, n is the valence of M, and Q is a hydrogen ion, an ammonium ion or an organic cation, or a mixture thereof. For purposes of the present invention, Y is preferably greater than 5 and less than about 50. Consequently, the silicon to aluminum atomic ratio in the above formula is greater than 5:1 and less than 100:1, and preferably greater than 5:1 and less than about 50:1.

It is also contemplated that other elements, such as gallium, boron and iron, can be variably substituted for aluminum in the above formula. Similarly, elements such as germanium and phosphorus can be variably substituted for silicon.

Suitable organic cations are those cations which are derived in aqueous solution from tetraethylammonium bromide or hydroxide, dibenzyl-1,4-diazabicyclo [2.2.2]octane chloride, dimethyldibenzyl ammonium chloride, 1,4-di(1-azonium bicyclo[2.2.2]octane)butane dibromide or dihydroxide, and the like. These organic cations are known in the art and are described, for example, in European Patent Applications Nos. 159,846 and 159,847, and U.S. Pat. No. 4,508,837. The preferred organic cation is the tetraethylammonium ion.

M is typically a sodium ion from the original synthesis but may also be a 5 metal ion added by ion exchange techniques. Suitable metal ions include those from Groups IA, IIA or IIIA of the Periodic Table or a transition metal. Examples of such ions include ions of lithium, potassium, calcium, magnesium, barium, lanthanum, cerium, nickel, platinum, palladium, and the like.

For high catalytic activity, the zeolite beta should be predominantly in its hydrogen ion form. Generally, the zeolite is converted to its hydrogen form by ammonium exchange followed by calcination. If the zeolite is synthesized with a high enough ratio of organonitrogen cation to sodium ion, calcination alone may be sufficient. It is preferred that, after calcination, a major portion of the cation sites are occupied by hydrogen ions and/or rare earth ions. It is especially preferred that at least 80% of the cation sites are occupied by hydrogen ions and/or rare earth ions.

The pure zeolite may be used as a catalyst, but generally it is preferred to mix the zeolite powder with an inorganic oxide binder such as alumina, silica, silica/alumina, or naturally occurring clays and form the mixture into tablets or extrudates. The final catalyst may contain from 1 to 99 wt. % zeolite beta. Usually the zeolite beta content will range from 10 to 90 wt. %, and more typically from 60 to 80 wt. %. The preferred inorganic binder is alumina. The mixture may be formed into tablets or extrudates having the desired shape by methods well known in the art. The extrudates or tablets will usually be cylindrical in shape. Other shapes with enhanced surface-to-volume ratios, such as fluted or polylobed cylinders, can be employed to enhance mass transfer rates and, thus, catalytic activity. Zeolite beta has a 12 ring structure with pore sizes of 5.5×5.5 Å and 7.6×6.4 Å. Zeolite beta is an intergrowth of three distinct, ordered polytypes (Higgins, et al., Zeolites, 8, 446 (1988); Treacy, et al., Nature, 332, 249 (1988). The pure polytypes are included within the scope of the term "zeolite beta", as used herein.

Whether the reaction takes place in a fixed bed or moving bed reactor or a catalyst bed within a catalytic distillation reactor, additional distillations are required to recover the product alkylbenzene. In the case where a fixed or moving bed reactor is used and where the reactants are ethylene and benzene, the unreacted ethylene, hydrogen, methane, ethane, unreacted benzene, and $C_6$–$C_7$ paraffins are removed in the overhead of a first distillation column. The bottoms of that column contain the product ethylbenzene and the polyalkylated benzenes. When the reaction is carried out in a catalytic distillation column, the above described separation takes place in the same distillation column where the catalyst is placed. In either case the following separations are carried out using conventional distillation columns using techniques known in the art. Several different arrangements of the subsequent distillation columns are possible, and within knowledge of persons of ordinary skill in the art.

In a preferred embodiment the bottoms stream containing the product ethylbenzene and the polyalkylated benzenes is separated by distillation into product ethylbenzene which goes overhead and the polyalkylated benzenes which are in the bottoms.

The vapor overhead contains unreacted ethylene and light paraffins. This unreacted ethylene from the ethylene-containing stream, if desired may be recovered by reaction with pure benzene in a second reactor or catalytic distillation tower. The condensed overhead product commonly known as a liquid distillate from the first distillation column, or the catalytic distillation column as the case may be, contains the unreacted $C_5$–$C_7$ paraffins and the small amount of unreacted benzene. A special feature of this invention is that use of a molar excess of ethylene results in high conversion of benzene such that a high percentage of the benzene contained in the benzene-containing feed stream is reacted. This benzene depleted stream may be sent to the gasoline pool while adding only an insignificant amount of benzene to the final gasoline product. A small stabilization tower may be required to strip off any remaining light materials.

Additional monoalkylated product may be produced from the polyalkylated material by transalkylation processes known in the art. The polyalkylated products may be reacted with additional aromatic feed in a separate reactor. In this embodiment, it is preferred to blend the bottoms from the distillation of monoalkylated product with a stoichiometric excess of a preferred aromatic feed, and react the mixture in a separate reactor over a suitable transalkylation catalyst. Suitable transalkylation catalysts include steam-stabilized Y zeolite and zeolite beta. The effluent from the transalkylation reactor is blended with alkylation reactor effluent and the combined stream distilled. A bleed may be taken from the polyalkylated product stream to remove unreactive heavies from the loop, or the polyalkylated product stream may be distilled to remove heavies prior to transalkylation.

Cumene is produced analogously to ethylbenzene, i.e., by a Friedel-Crafts alkylation of benzene with propylene. The present invention may be used with a molar excess of propylene to benzene, both in dilute streams. These dilute streams are reacted using a zeolite beta catalyst wherein a mixture of cumene, di and tri isopropyl benzene will be produced. Diisopropylbenzene and triisopropylbenzene can then be transalkylated to cumene with additional benzene. The stream containing benzene will preferably be chosen from amongst the same streams mentioned for the production of ethylbenzene. The stream containing propylene can be preferably chosen from the dilute propylene streams available in refineries and chemical plants. Examples include dilute propylene from catalytic cracking units and steam crackers. Another embodiment would include the use of a $C_3$ minus cut (all molecules boiling at or below propane and propylene) from these sources.

The following examples are provided to further illustrate the invention in accordance with the principles described, but are not to be construed as limiting the invention in any way except as indicated by the claims.

EXAMPLE 1

This Example shows the alkylation of benzene with a stoichiometric quantity of ethylene in a continuous reaction over a zeolite beta catalyst. Good catalyst activity maintenance is found compared to a prior art zeolite catalyst (see Example 2). Also, good selectivity to ethylbenzene, diethylbenzene, and triethylbenzene is found, with little tetraethylbenzene and higher alkylate.

Dry benzene (54.6 g/h; 0.70 mole/h) and ethylene (0.24 std L/min; 0.64 mole/h) were fed to a 300 cc stirred (750 rpm) autoclave reactor held at 200° C. The solid catalyst (15.6 g) was held in a fixed basket formed of two concentric cylinders of steel mesh (Robinson-Mahoney reactor). The autoclave stirrer is designed to circulate both liquid and gas through the catalyst basket. This results in isothermal reaction conditions with good mass transfer to the catalyst particles. The liquid level in the reactor was held constant by a standpipe that extended to a point above the catalyst basket. Both liquid and gas exited the reactor through this standpipe and then through a back-pressure regulator that held the total pressure in the reactor at 140 psig. These liquid and gas streams were separated in a small vessel at 20 psig pressure. The gas stream (nearly all ethylene) was analyzed periodically by a gas chromatograph. Samples of the liquid product stream were collected periodically, and were also analyzed on a gas chromatograph. Gas volume was measured with a wet test meter. The accumulated weight of liquid product was recorded.

The catalyst used in this Example was zeolite beta, obtained from UOP in the form of 1/16 inch extrudates. Content of the extrudates was 70% zeolite beta and 30% inorganic binder. The catalyst was received in the hydrogen form and confirmed as zeolite beta by x-ray diffraction. Before use it was dried overnight under vacuum at 200° C. When the catalyst was placed in the reactor it was covered with an initial charge of ethylbenzene in order to keep the catalyst wetted during heatup to reaction temperature. After the reactor reached temperature, the flow of both benzene and ethylene was started.

Results are shown in Table I, where the composition of the liquid product in weight % is shown as the run progressed. Note that the catalyst maintained good activity during the 100 hour run, and was selective to a mixture of ethylbenzene, diethylbenzene, and triethylbenzene. The spent catalyst particles were a uniform light brown; fresh catalyst is tan.

TABLE I

Liquid Product Composition (wt %)

| Time onstream (hours) | Benzene | EB | diEB | triEB | tetra-, penta- & hexaEB | other alkylate |
|---|---|---|---|---|---|---|
| 6 | 32.0 | 33.6 | 22.8 | 9.4 | 1.6 | 0.60 |
| 14 | 39.9 | 30.1 | 19.8 | 8.3 | 1.4 | 0.50 |
| 22 | 40.7 | 29.7 | 19.4 | 8.1 | 1.3 | 0.50 |
| 30.25 | 40.9 | 29.3 | 19.4 | 8.3 | 1.4 | 0.50 |
| 38.5 | 40.8 | 29.7 | 19.4 | 8.3 | 1.4 | 0.50 |
| 46.25 | 42.2 | 29.3 | 18.8 | 8.0 | 1.3 | 0.50 |
| 55 | 45.5 | 28.3 | 17.2 | 7.0 | 1.1 | 0.40 |
| 63 | 44.0 | 28.3 | 18.1 | 7.8 | 1.3 | 0.50 |
| 70.5 | 47.8 | 28.0 | 15.9 | 6.2 | 0.9 | 0.30 |
| 78 | 40.3 | 30.2 | 19.3 | 8.3 | 1.4 | 0.50 |
| 86 | 44.6 | 28.7 | 17.7 | 7.4 | 1.2 | 0.40 |
| 94 | 46.5 | 27.3 | 17.0 | 7.4 | 1.2 | 0.50 |
| 100 | 48.0 | 27.4 | 16.1 | 6.5 | 1.0 | 0.40 |

COMPARATIVE EXAMPLE 2

This Example was conducted in exactly the same manner as Example 1, except the catalyst used was a steam-stabilized Y zeolite. This is the catalyst currently used in at least two commercially available technologies for the reaction of ethylene with benzene to form ethylbenzene. However, these technologies use a large molar excess of benzene over ethylene in the feed to the reactor. This Comparative Example shows that this prior art catalyst is not suitable for reaction of benzene with a stoichiometric or excess molar quantity of ethylene.

The steam-stabilized Y zeolite catalyst was received from UOP, and is designated LZY-84 (formerly designated LZY-82). The LZY-84 was in the form of 1/16 inch extrudates, which contained 20% inorganic binder. The base zeolite has a silica to alumina molar ratio of 5.3. The zeolite was received in the hydrogen form, and was dried under vacuum at 200° C. overnight before use. As in the previous Example, the catalyst (17.9 g) was covered with ethylbenzene when it was loaded in the reactor, in order to keep it wetted during initial heatup to 200° C. at the imposed total pressure of 140 psig.

The results are shown in Table II, where the composition of the liquid product in weight % is shown as the run progressed. The catalyst activity for production of ethylbenzene, diethylbenzene, and triethylbenzene rapidly declined, and the run was terminated after only 28 hours. The spent catalyst particles were very dark, either purple or nearly black; fresh catalyst is tan.

TABLE II

Liquid Product Composition (wt %)

| Time onstream (hours) | Benzene | EB | diEB | triEB | tetra-, penta- & hexaEB | other alkylate |
|---|---|---|---|---|---|---|
| 4.4 | 51.2 | 27.8 | 13.0 | 4.5 | 1.7 | 1.90 |
| 6.7 | 60.6 | 22.4 | 9.4 | 3.5 | 1.8 | 2.20 |
| 10.7 | 68.2 | 20.1 | 6.7 | 2.3 | 1.0 | 1.70 |
| 14.7 | 81.5 | 12.2 | 3.6 | 1.2 | 0.4 | 1.20 |
| 18.7 | 80.5 | 12.0 | 3.8 | 1.5 | 0.7 | 1.60 |
| 22.3 | 86.5 | 6.9 | 2.4 | 1.4 | 0.7 | 1.60 |
| 28.4 | 88.0 | 4.6 | 0.7 | 0.8 | 3.9 | 2.00 |

EXAMPLE 3

This Example was conducted in the same manner as Example 1, except the zeolite beta catalyst was from a different source. The benzene feed rate was 54.6 g/h (0.70 mole/h) and the ethylene feed rate was 0.26 std L/min (0.70 mole/h). The reaction temperature was 200° C. and the total pressure was 140 psig. The zeolite beta (12.9 g) was obtained from PQ Corporation in the form of 1/16 inch extrudates which were 80% zeolite beta and 20% alumina binder. The silica to alumina ratio of the zeolite beta was 50:1. The zeolite was received in the hydrogen form and confirmed as zeolite beta by x-ray diffraction. It was dried under vacuum at 200° C. overnight before use.

The results are shown in Table III. Again, good activity maintenance was found over the 100 hour run. Also, good selectivity to ethylbenzene, diethylbenzene, and triethylbenzene was found.

TABLE III

Liquid Product Composition (wt %)

| Time onstream (hours) | Benzene | EB | diEB | triEB | tetra-, penta-& hexaEB | other alkylate |
|---|---|---|---|---|---|---|
| 5.67 | 39.9 | 27.2 | 19.9 | 10.4 | 2.2 | 0.30 |
| 13.67 | 40.1 | 27.2 | 19.9 | 10.3 | 2.2 | 0.30 |
| 21.25 | 41.2 | 26.8 | 19.3 | 10.0 | 2.2 | 0.30 |
| 28.25 | 40.7 | 26.7 | 19.5 | 10.2 | 2.2 | 0.30 |
| 36.25 | 41.5 | 26.8 | 19.3 | 10.0 | 2.1 | 0.30 |
| 48.5 | 41.2 | 26.9 | 19.4 | 10.1 | 2.2 | 0.30 |
| 52.5 | 40.7 | 26.7 | 19.6 | 10.4 | 2.3 | 0.30 |
| 60.5 | 42.4 | 26.3 | 18.9 | 10.0 | 2.2 | 0.30 |
| 68.5 | 43.4 | 26.0 | 18.4 | 9.7 | 2.1 | 0.30 |
| 77 | 40.9 | 26.9 | 19.4 | 10.3 | 2.3 | 0.30 |
| 85 | 43.3 | 25.9 | 18.6 | 9.8 | 2.1 | 0.30 |
| 93 | 43.1 | 25.6 | 18.6 | 10.1 | 2.2 | 0.30 |
| 100 | 46.6 | 25.2 | 17.0 | 8.9 | 1.9 | 0.20 |

EXAMPLE 4

This Example shows the reaction of a stoichiometric amount of ethylene with benzene at 180° C. using the same charge of zeolite beta catalyst used in Example 3. The benzene feed rate was 28.3 g/h (0.36 mole/h) and the ethylene feed rate was 0.14 std L/min (0.38 mole/h). The total pressure was 100 psig. The results are shown in Table IV. Good activity maintenance was found over the 100 hour run. Also, good selectivity to ethylbenzene, diethylbenzene, and triethylbenzene was found. The spent catalyst was a darker tan than the fresh catalyst.

TABLE IV

Liquid Product Composition (wt %)

| Time onstream (hours) | Benzene | EB | diEB | triEB | tetra-, penta-& hexaEB | other alkylate |
|---|---|---|---|---|---|---|
| 9.5 | 35.9 | 29.0 | 21.9 | 10.8 | 2.2 | 0.20 |
| 17.5 | 36.2 | 28.1 | 21.8 | 11.2 | 2.4 | 0.20 |
| 24.5 | 37.5 | 27.6 | 21.1 | 10.9 | 2.4 | 0.20 |
| 29 | 37.0 | 27.6 | 21.2 | 11.2 | 2.5 | 0.20 |
| 37.5 | 37.5 | 27.4 | 21.1 | 11.2 | 2.5 | 0.20 |
| 45.5 | 37.1 | 26.8 | 21.3 | 11.7 | 2.7 | 0.20 |
| 53.5 | 36.2 | 26.8 | 21.7 | 12.0 | 2.7 | 0.20 |
| 62 | 35.9 | 27.9 | 22.1 | 11.5 | 2.5 | 0.20 |
| 69.7 | 39.2 | 27.1 | 20.4 | 10.7 | 2.3 | 0.20 |
| 77.5 | 37.9 | 26.7 | 21.0 | 11.4 | 2.6 | 0.20 |
| 85.7 | 39.9 | 26.9 | 19.9 | 10.5 | 2.4 | 0.20 |
| 93.7 | 40.1 | 27.5 | 20.0 | 10.0 | 2.1 | 0.20 |
| 100 | 42.1 | 26.6 | 19.2 | 9.7 | 2.0 | 0.10 |

EXAMPLE 5

This Example was conducted in the same manner as Example 1. The zeolite beta catalyst (15.1 g) was from the same source. The benzene feed rate was 54.6 g/h (0.70 mole/h) and the ethylene feed rate was 0.355 std L/min (0.95 mole/h). The reaction temperature was 200° C. and the total pressure was 170 psig. In this Example the catalyst was not covered with an initial charge of ethylbenzene (as in Examples 1–4) since it had already been run under a different set of conditions and remained wetted during heatup.

The results are shown in Table V. Good activity maintenance was found over the 45 hour run. Good selectivity to ethylbenzene, diethylbenzene, and triethylbenzene was found.

TABLE V

Liquid Product Composition (wt %)

| Time (hours) | Benzene | EB | diEB | triEB | tetra-, penta-& hexaEB | other alkylate |
|---|---|---|---|---|---|---|
| 13.1 | 46.3 | 24.0 | 15.3 | 10.5 | 3.0 | 0.9 |
| 21.1 | 50.0 | 23.6 | 13.9 | 9.0 | 2.3 | 0.7 |
| 29.1 | 48.6 | 23.4 | 14.4 | 9.9 | 2.8 | 0.9 |
| 37.1 | 49.8 | 22.8 | 14.0 | 9.7 | 2.8 | 0.8 |
| 45.1 | 52.1 | 22.6 | 13.1 | 8.8 | 2.5 | 0.7 |

EXAMPLE 6

This Example shows the use of both a dilute stream of benzene (5% benzene in hexanes) and a dilute stream of ethylene (ethylene in hydrogen). It was conducted in the same manner as Example 1, except the catalyst was not covered with an initial charge of ethylbenzene. The zeolite beta catalyst (15.5 g) was from the same source. The contained benzene feed rate was initially 6.14 g/h (0.079 mole/h) and later increased to 6.25 g/h (0.080 mole/h), while the contained hexanes feed rate was 112 g/h. The ethylene feed rate was 30.0 std cc/min (0.080 mole/h) while the hydrogen feed rate was 70 std cc/min. The reaction temperature was 180° C. and the total pressure was 250 psig.

The results are shown in Table VI. Good activity maintenance was found over the 71 hour run. Good selectivity to ethylbenzene, diethylbenzene, and triethylbenzene was found.

TABLE VI

Liquid Product Composition (wt %)

| Time (hours) | Benzene | EB | diEB | triEB | tetra-, penta-& hexaEB | other alkylate |
|---|---|---|---|---|---|---|
| 10.8 | 3.1 | 1.5 | 1.0 | 0.6 | 0.2 | 0.3 |
| 15.3 | 3.1 | 1.4 | 0.9 | 0.5 | 0.2 | 0.2 |
| 24.5 | 3.1 | 1.7 | 1.0 | 0.6 | 0.2 | 0.3 |
| 28 | 3.4 | 1.5 | 1.0 | 0.5 | 0.2 | 0.2 |
| 34 | 3.4 | 1.6 | 1.1 | 0.6 | 0.2 | 0.2 |
| 42 | 3.3 | 1.5 | 1.1 | 0.6 | 0.2 | 0.3 |
| 45 | 3.4 | 1.5 | 1.0 | 0.6 | 0.2 | 0.2 |
| 49 | 3.4 | 1.5 | 1.0 | 0.6 | 0.2 | 0.2 |
| 55 | 3.5 | 1.6 | 1.1 | 0.6 | 0.2 | 0.2 |
| 63 | 3.5 | 1.6 | 1.0 | 0.6 | 0.2 | 0.2 |
| 71 | 3.5 | 1.6 | 1.1 | 0.6 | 0.2 | 0.2 |

EXAMPLE 7

This Example is identical to Example 6, except it uses a zeolite beta catalyst (16.1 g) from the same source as in Example 3. The contained benzene feed rate was initially 6.61 g/h (0.085 mole/h) and later increased to 6.64 g/h (0.085 mole/h), while the contained hexanes feed rate was 111 g/h. The ethylene feed rate was 31.5 std cc/min (0.84 mole/h) while the hydrogen feed rate was 70 std cc/min. The reaction temperature was 180° C. and the total pressure was 250 psig.

The results are shown in Table VII. Good activity maintenance was found over the 104 hour run. Good selectivity to ethylbenzene, diethylbenzene, and ethylbenzene was found.

TABLE VII

Liquid Product Composition (wt %)

| Time (hours) | Benzene | EB | diEB | triEB | tetra-, penta- & hexaEB | other alkylate |
|---|---|---|---|---|---|---|
| 6.33 | 3.5 | 1.6 | 1.1 | 0.7 | 0.2 | 0.2 |
| 14.33 | 3.5 | 1.5 | 1.0 | 0.7 | 0.2 | 0.2 |
| 22.33 | 3.5 | 1.6 | 1.0 | 0.7 | 0.2 | 0.0 |
| 29.75 | 3.7 | 1.7 | 1.1 | 0.7 | 0.2 | 0.2 |
| 38.75 | 3.6 | 1.6 | 1.0 | 0.7 | 0.2 | 0.2 |
| 46.22 | 3.4 | 1.6 | 1.0 | 0.7 | 0.3 | 0.2 |
| 51.33 | 3.4 | 1.6 | 1.1 | 0.8 | 0.3 | 0.2 |
| 66.33 | 3.1 | 1.4 | 1.2 | 1.1 | 0.6 | 0.3 |
| 74 | 3.4 | 1.6 | 1.1 | 0.9 | 0.3 | 0.2 |
| 82 | 3.4 | 1.5 | 1.0 | 0.7 | 0.2 | 0.2 |
| 90 | 3.5 | 1.5 | 0.9 | 0.6 | 0.2 | 0.2 |
| 98 | 3.4 | 1.5 | 1.0 | 0.7 | 0.2 | 0.2 |
| 104 | 3.4 | 1.5 | 1.0 | 0.7 | 0.2 | 0.2 |

EXAMPLE 8

This Example is a computer simulation that demonstrates the recovery of benzene from a dilute stream as a mixture of ethylbenzene, diethylbenzene, and triethylbenzene, by reaction with a molar excess of ethylene contained in a dilute stream, and using a zeolite beta catalyst. Table VIII provides feed and product compositions for this example. The benzene-containing stream (9,000 kg/h total) is representative of a reformate heartcut which is hydrogenated in order to remove the small amount of olefins. It is 35.6% benzene by weight with the balance predominantly $C_6$ alkanes, and is essentially free of toluene. The ethylene-containing stream (9,100 kg/h total) is representative of what can be obtained from a fluid catalytic cracking unit and additionally contains ethane, methane, hydrogen, nitrogen, and other species lighter than ethane and ethylene. The stream is purified to remove species such as hydrogen sulfide, carbon dioxide, and ammonia. The stream contains 37.8% ethylene by weight and is essentially free of propylene and other species heavier than ethane.

The reaction proceeds in a distillation tower that contains 17,600 kg of zeolite beta catalyst incorporated in a packing structure. The catalyst section achieves eleven theoretical distillation stages in the simulation. The two feed streams enter the tower at the bottom of the catalyst section. The molar ratio of ethylene to benzene contained in the two feed streams is 3.0. The imposed total pressure on the reactive distillation tower is 17.9 $kg/cm^2$. Experimentally derived kinetic constants for the reaction of benzene with ethylene over a zeolite beta catalyst are used in the simulation. The calculated temperature at the bottom of the zeolite packing in the tower is 182° C. and at the top is 185° C. Three theoretical trays are present in the tower above the zeolite packing, and a molar reflux ratio of 0.6 is used (defined as reflux/total distillate). Inert $C_6$ alkanes from the benzene stream are removed at the top of the tower, as is the partially depleted ethylene-containing stream. Benzene conversion is 95.9%, as a mixture of ethylbenzene (40.4 wt. %), diethylbenzene (52.6 wt. %), triethylbenzene (5.3 wt. %), and tetraethylbenzene (1.7 wt. %) that is removed at the bottom of the tower. Additional distillation trays are required below the catalyst section to "strip" benzene and other $C_6$'s from the bottoms product. The remainder of the ethylene in the ethylene-containing stream can be recovered if desired by reaction with pure benzene in a second catalytic distillation tower. The ethylbenzene product may be recovered by distillation, and the diethylbenzene, triethylbenzene, and tetraethylbenzene may be converted to additional ethylbenzene by transalkylation with excess benzene using processes well known in the art.

TABLE VIII

Feed and Product Compositions for Example 8

| Composition, wt % | Benzene Containing Feed | Ethylene Containing Feed | Overhead Vapor Distillate | Overhead Liquid Distillate | Bottoms Alkylate Product |
|---|---|---|---|---|---|
| Hydrogen | | | 3.7 | 4.7 | |
| Methane | | | 36.6 | 47.1 | |
| Ethylene | | | 37.8 | 20.2 | |
| Ethane | | | 21.9 | 28.0 | |
| $C_6$–C7 nonaromatics | 64.4 | | | 98.7 | |
| Benzene | 35.6 | | | 1.3 | |
| Ethylbenzene | | | | | 40.4 |
| Di-ethylbenzene | | | | | 52.6 |
| Tri-ethylbenzene | | | | | 5.3 |
| Tetra-ethylbenzene | | | | | 1.7 |
| Total Flow Rate (kg/h) | 9,000 | 9,100 | 8,285 | 5,942 | 5,023 |

Although the present invention has been described in considerable detail with reference to certain preferred embodiments, other embodiments are possible. Therefore, the spirit and scope of the appended claims should not be limited to the description of the preferred embodiments contained herein.

What is claimed is:

1. A process for the alkylation of an aromatic hydrocarbon contained in a hydrocarbon stream comprising:

(a) separating essentially all aromatics other than said aromatic hydrocarbon from said hydrocarbon stream, thereby forming an aromatic-rich stream;

(b) treating said aromatic-rich stream of (a) by converting essentially all olefinic compounds contained therein by hydrogenation;

(c) contacting the thus treated aromatic-rich stream from (b) with an olefin-containing stream comprising at least one olefin selected from the group consisting of ethylene, propylene, and butylene, wherein the molar ratio of the olefin(s) to said aromatic hydrocarbon is not less than 1 in the presence of a catalyst comprising zeolite beta, under alkylation conditions, whereby mono and polyalkylated aromatics are formed; and (d) separating said mono and polyalkylated aromatics formed in (c) from the remaining hydrocarbons.

2. The process in claim 1, wherein said aromatic hydrocarbon is a single ring aromatic hydrocarbon.

3. The process in claim 1, wherein the contacting in (c) is done in the presence of both a liquid and a vapor phase.

4. The process in claim 1, wherein (c) takes place in a distillation tower.

5. The process in claim 1, wherein said olefin-containing stream comprises ethylene and propylene and essentially no other olefins.

6. The process in claim 1, wherein the molar ratio of the olefin to the aromatic hydrocarbon is greater than 1.

7. The process in claim 1, wherein the molar ratio of the olefin to the aromatic hydrocarbon is greater than 1.1.

8. A process for ethylating benzene contained in a hydrocarbon stream comprising:

(a) separating substantially all aromatics other than benzene from said hydrocarbon stream, thereby forming a benzene-rich stream;

(b) treating said benzene-rich stream of (a) by converting essentially all olefinic compounds contained therein by hydrogenation;

(c) contacting the thus treated benzene-rich stream of (b) with an olefin stream comprising ethylene and essentially no other olefin wherein the molar ratio of ethylene to benzene is not less than 1, in the presence of a catalyst comprising zeolite beta under alkylation conditions, whereby mono and polyethyl benzenes are formed; and (d) separating the mono and polyethyl benzenes formed in (c) from the remaining hydrocarbons.

9. The process in claim 8, wherein said contacting is done in the presence of both a liquid and vapor phase.

10. The process in claim 8, wherein aromatics with a higher boiling point than benzene are removed by fractional distillation.

11. The process in claim 8, wherein (c) takes place in a distillation tower.

12. The process in claim 8, wherein the molar ratio of said ethylene to said benzene is greater than 1.

13. The process in claim 8 wherein the molar ratio of said ethylene to said benzene is greater than 1.1.

14. The process in claim 8, wherein the molar ratio of aromatics with higher boiling point than benzene to benzene is less than about 0.01.

15. The process in claim 8, wherein the alkylation reaction takes place at from about 100 degrees Centigrade to 300 degrees Centigrade, and a pressure from about 30 to about 500 psia.

16. The process in claim 8, wherein the hydrocarbon stream containing benzene is a light reformate.

17. The process in claim 8, wherein the hydrocarbon stream containing benzene is a pyrolysis gasoline.

18. The process in claim 8, wherein the stream comprising ethylene is the dry gas from the overhead of a catalytic cracker deethanizer.

19. The process in claim 8, wherein the stream comprising ethylene is the feed to a steam cracker ethylenelethane splitter.

20. The process in claim 8, wherein said olefin stream comprising ethylene is a stream containing $C_2$ and lower boiling components.

21. The process in claim 8, wherein the ethylbenzene is separated from the polyethylbenzene and said polyethylbenzene is then transalkylated with benzene to form ethylbenzene.

22. A process for ethylating benzene contained in a reformate benzene heartcut stream comprising:

(a) treating said reformate benzene heartcut stream with hydrogen to convert essentially all olefinic compounds to paraffins, thereby forming a benzene-rich stream;

(b) contacting said benzene-rich stream with an olefin stream comprising ethylene and essentially no other olefins wherein the molar ratio of ethylene to benzene is not less than 1, in the presence of a catalyst comprising zeolite beta under alkylation conditions, whereby mono and polyethyl benzenes are formed;

(c) separating the ethylbenzene and polyethyl benzenes formed in (b) from the remaining hydrocarbons; and (d) separating the ethylbenzene from the polyethyl benzene.

23. The process in claim 22, wherein (b) takes place in a distillation tower.

24. The process in claim 22, wherein said contacting is done in the presence of both a liquid and a vapor phase.

25. The process in claim 22, wherein the molar ratio of ethylene to benzene is greater than 1.

26. The process in claim 22, wherein the molar ratio of ethylene to said benzene is greater than 1.1.

27. The process in claim 22, wherein the alkylation reaction takes place from about 100 degrees Centigrade to 300 degrees Centigrade, and a pressure from about 30 psia to about 500 psia.

28. The process in claim 22, wherein said olefin stream comprising ethylene is the dry gas from the overhead of a catalytic cracker deethanizer.

29. The process in claim 22, wherein said olefin stream comprising ethylene is the feed to a steam cracker ethylene/ethane splitter.

30. The process in claim 22, wherein the polyethyl benzenes are then transalkylated with benzene to form ethylbenzene.

31. A process for alkylating benzene contained in a hydrocarbon stream comprising:

(a) separating substantially all aromatics other than benzene from the hydrocarbon stream, thereby forming a benzene-rich stream;

(b) treating said benzene-rich stream of (a) by converting essentially all olefinic compounds contained therein by hydrogenation;

(c) contacting the thus treated benzene-rich stream of (b) with an olefin stream comprising propylene wherein the molar ratio of propylene to benzene is not less than 1, in the presence of a catalyst comprising zeolite beta under alkylation conditions, whereby mono and polyisopropyl-benzenes are formed; and (d) separating the mono and polyisopropylbenzenes formed in (c) from the remaining hydrocarbons.

32. The process in claim 31, wherein said contacting is done in the presence of both a liquid and vapor phase.

33. The process in claim 31, wherein the aromatics with other than benzene are removed by fractional distillation.

34. The process in claim 31, wherein (c) takes place in a distillation tower.

35. The process in claim 31, wherein the molar ratio of said propylene to said benzene is greater than 1.

36. The process in claim 31, wherein the molar ratio of said propylene to said benzene is greater than 1.1.

37. The process in claim 31, wherein the molar ratio of aromatics with higher boiling point than benzene to benzene is less than about 0.01.

38. The process in claim 31, wherein the alkylation reaction takes place at from about 100 degrees Centigrade to 300 degrees Centigrade, and a pressure from about 30 to about 500 psi.

39. The process in claim 31, wherein the hydrocarbon stream containing benzene is a light reformate.

40. The process in claim 31, wherein the hydrocarbon stream containing benzene is a pyrolysis gasoline.

41. The process in claim 31: wherein said olefin stream comprising propylene is the overhead of a catalytic cracker depropanizer.

42. The process in claim 31, wherein said olefin stream comprising propylene is the feed to a propane/propylene splitter.

43. The process in claim 31, wherein said olefin stream comprising propylene is a stream containing $C_3$ and lower boiling components.

44. The process in claim 1, wherein said aromatic hydrocarbon is benzene, and said aromatic-rich stream is diluted benzene containing at least 10 wt. % benzene.

45. The process in claim 1, wherein said zeolite beta has forms selected from the group consisting of crystalline aluminosilicates having the empirical formula:

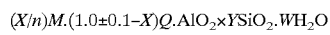

$$(X/n)M.(1.0\pm0.1-X)Q.AlO_2 \cdot xYSiO_2 \cdot WH_2O$$

wherein X is less than 1, Y is greater than 5 and less than 100, W is up to about 4.

* * * * *